United States Patent
Connelly et al.

(10) Patent No.: US 6,554,522 B1
(45) Date of Patent: Apr. 29, 2003

(54) TOOTHBRUSH AND PACKAGING

(76) Inventors: Jason Connelly, P.O. Box 224, Lava Hot Springs, ID (US) 83246; Cynthia Deborah Paulk, 366 N. 2$^{nd}$ East, Soda Springs, ID (US) 83276

( * ) Notice: Subject to any disclaimer, the term of this patent is extended or adjusted under 35 U.S.C. 154(b) by 34 days.

(21) Appl. No.: 10/092,765

(22) Filed: Mar. 6, 2002

(51) Int. Cl.$^7$ ................................................ A46B 11/04
(52) U.S. Cl. ........................ 401/272; 401/176; 401/195; 401/268; 401/286; 132/308; 206/361
(58) Field of Search .................. 401/143, 146, 401/149, 150, 176–182, 195, 268, 270, 272, 286; 15/167.1; 132/308, 309; 206/361, 362

(56) References Cited

U.S. PATENT DOCUMENTS

| | | | | |
|---|---|---|---|---|
| 3,589,823 A | * | 6/1971 | Hendrickson | 401/176 |
| 4,139,312 A | * | 2/1979 | Marano et al. | 401/176 |
| 4,865,481 A | * | 9/1989 | Scales | 401/195 |
| 5,139,142 A | * | 8/1992 | Simon | 206/361 |
| 5,184,719 A | * | 2/1993 | Gordon | 132/309 |
| 5,403,105 A | * | 4/1995 | Jameson | 401/268 |
| 5,755,523 A | * | 5/1998 | Seydel | 401/176 |
| 5,769,553 A | * | 6/1998 | Chaudhri et al. | 401/195 |
| 5,865,195 A | * | 2/1999 | Carter | 132/309 |
| 5,893,378 A | * | 4/1999 | Llerena | 401/268 |
| 6,039,050 A | * | 3/2000 | Goldenberg | 132/309 |
| 6,397,859 B1 | * | 6/2002 | Byrd | 132/308 |
| 6,397,860 B1 | * | 6/2002 | Hill, II | 132/309 |

FOREIGN PATENT DOCUMENTS

| | | | |
|---|---|---|---|
| GB | 2175798 A | * 12/1986 | 401/176 |

* cited by examiner

*Primary Examiner*—David J. Walczak
*Assistant Examiner*—Tuan Nguyen

(57) ABSTRACT

A toothbrush. In a first embodiment, a plunger is located within a chamber in the head of the toothbrush. Pushing the plunger farther into the head forces toothpaste that will have been placed within the chamber through apertures in the first side of the head of the toothbrush onto bristles that are attached to such first side. Preferably, a removable wrapper covers the head of the toothbrush. In a second embodiment, a pliable pouch is sealingly attached to a second side of the head; and the apertures run from the first side of the head to the second side of the head. Preferably, a rupturable material cover is attached either to the first side or the second side of the head. A second end of the handle of the toothbrush is curved and adapted for attachment of dental floss under tension. Packaging contains the other elements of the toothbrush in a first end and mouthwash, gum, a breath mint, or a quantity of water in a second end.

12 Claims, 4 Drawing Sheets

TOOTHBRUSH AND PACKAGING

BACKGROUND OF THE INVENTION

1. Field of the Invention

This invention relates to a toothbrush and packaging therefor which, in one embodiment, also contains powdered mouthwash and which can function as a container for mixing such powdered mouthwash with water and using the resultant liquid mouthwash.

2. Description of the Related Art

A multitude of patents exist for toothbrushes.

Many of these, e.g., U.S. Pat. Nos. 5,769,553 and 6,039,050, provide for supplying toothpaste to the bristles through an aperture in the base of the head of the toothbrush, upon which base the bristles are mounted. The present inventor is, however, unaware of any such patent wherein the movement of the toothpaste results from a plunger having folding flaps which fit into one or more channels in a chamber within which the plunger is mounted to preclude removal of the plunger from such chamber. Similarly, the present inventor knows of no patent for a toothbrush where the toothpaste is located within a pliable pouch attached to a second side of the base of the head in such a manner as to preclude air from contacting the toothpaste and to permit the toothpaste, when pressure is applied to the pliable pouch, to flow through the apertures in such base. Although U.S. Pat. No. 5,769,553 has the toothpaste in a pouch that is pierced immediately prior to the toothpaste being forced toward the apertures in the base of the head of the toothbrush and although one embodiment of U.S. Pat. No. 6,039,050 has a plastic sheet that seals only the end of the chamber containing toothpaste from which a handle is inserted to force toothpaste from the head, neither of these patents covers the aperture or apertures from which the toothpaste reaches the bristles with a thin membrane to keep the toothpaste fresh.

Several patents, e.g., U.S. Pat. Nos. 4,865,481; 5,769,553; and 5,893,378 also have dental floss associated with the handle of a toothbrush. Moreover, in the devices of U.S. Pat. Nos. 5,184,719; 5,365,956; and 6,039,050, dental floss is attached to the toothbrush so that such dental floss spans a curved portion of the toothbrush.

Also, a number of patents, e.g., U.S. Pat. Nos. 4,865,481; 5,769,553; and 5,893,376, have embodiments which include a liquid mouthwash contained within some portion of a toothbrush. As far as the present inventor is aware, however, none of these patents apply to the use of powdered mouthwash.

The head and toothpaste-coated bristles of the toothbrush in U.S. Pat. No. 5,184,719 are vacuum sealed within a package, but no provision is made to store the toothpaste in conjunction with the toothbrush prior to the application of such toothpaste to the bristles.

Packages which contain a toothbrush and toothpaste are covered by U.S. Pat. Nos. 6,062,233 and 6,135,274. The package of the latter patent has a inner container which can be ruptured to place the toothpaste upon the bristles of the toothbrush. The packages of U.S. Pat. Nos. 4,530,129 and 6,105,586 also contain dental floss. None of these packages, however, contain mouthwash, especially a powdered mouthwash. And none of these packages have a portion that may be used to mix the powdered mouthwash with water and to facilitate the use of such mixed mouthwash.

SUMMARY OF THE INVENTION

The toothbrush of the present invention supplies toothpaste to the bristles through one or more apertures in the base of the head of the toothbrush, upon a first side of which base the bristles are mounted.

In a first embodiment, this is the result of a plunger being pushed into a chamber which communicates with the one or more apertures. The plunger has one or more folding flaps which fit into one or more channels in a chamber within which the plunger is mounted to preclude removal of the plunger from such chamber. The head of the toothbrush is preferably sealed within a removable vacuum-sealed wrapper in order to keep the toothpaste fresh and prevent the plunger from being pushed farther into the chamber until it is desired to use the toothbrush.

In a second embodiment, a pliable pouch is attached to a second side of the base of the head in such a manner as to preclude air from contacting the toothpaste and to permit the toothpaste, when pressure is applied to the pliable pouch, to flow from such pouch through the one or more apertures in the base. A thin membrane that will rupture as the toothpaste is forced toward the apertures preferably covers the aperture or apertures from which the toothpaste reaches the bristles in order to keep the toothpaste fresh.

The packaging for the toothbrush has a first end and a second end.

The second end of the packaging is removably attached to the remained of the packaging and is constructed to contain powdered mouthwash preferably but, optionally, gum, a breath mint, or a quantity of water.

The first end of the packaging is built to enable the powdered mouthwash to be mixed with water in such first end and then to be utilized.

DESCRIPTION OF THE PREFERRED EMBODIMENT

Figure 1:
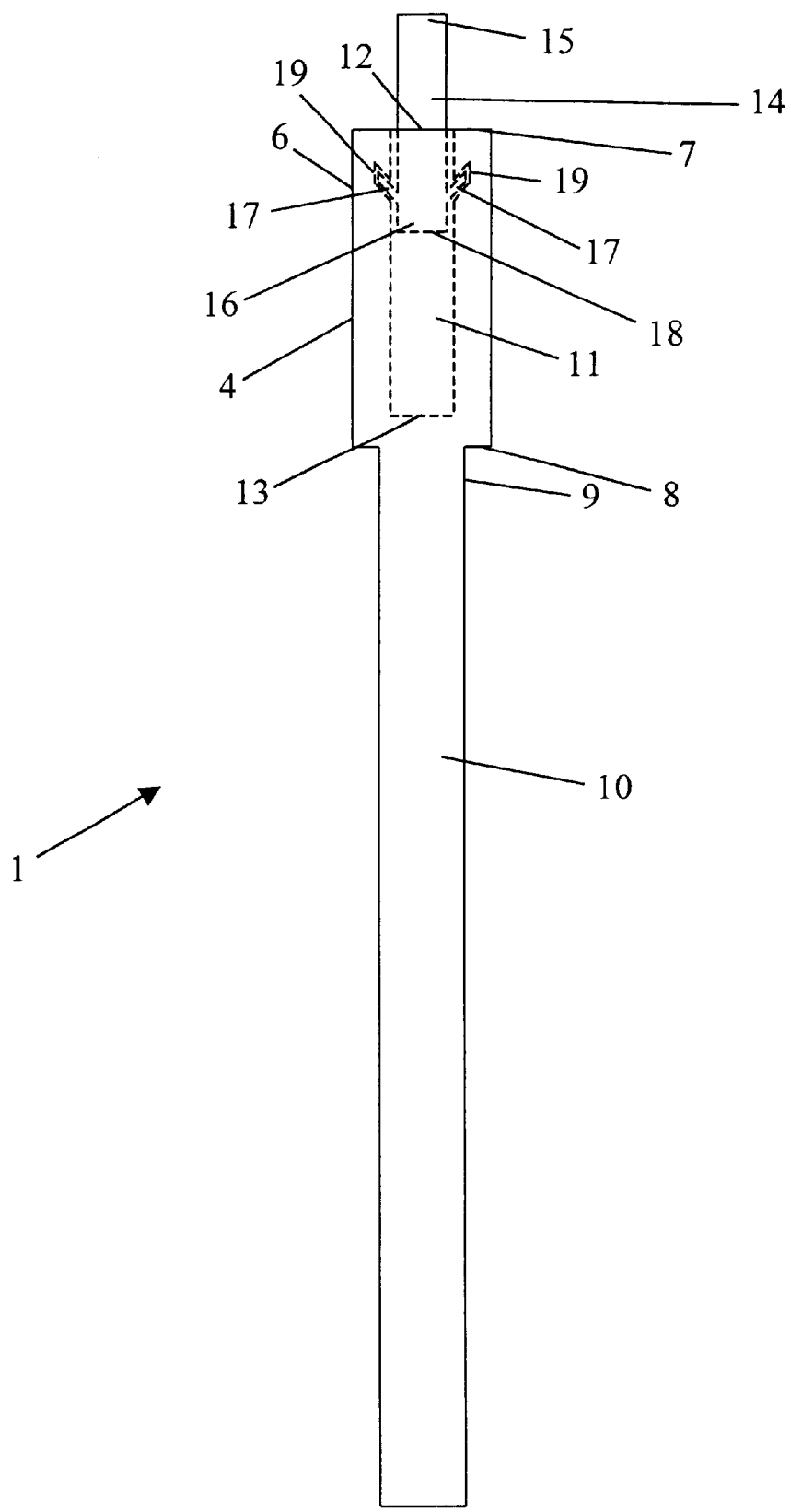
FIG. 1 is a plan view from the reverse side of the first embodiment for the toothbrush.
Figure 2:
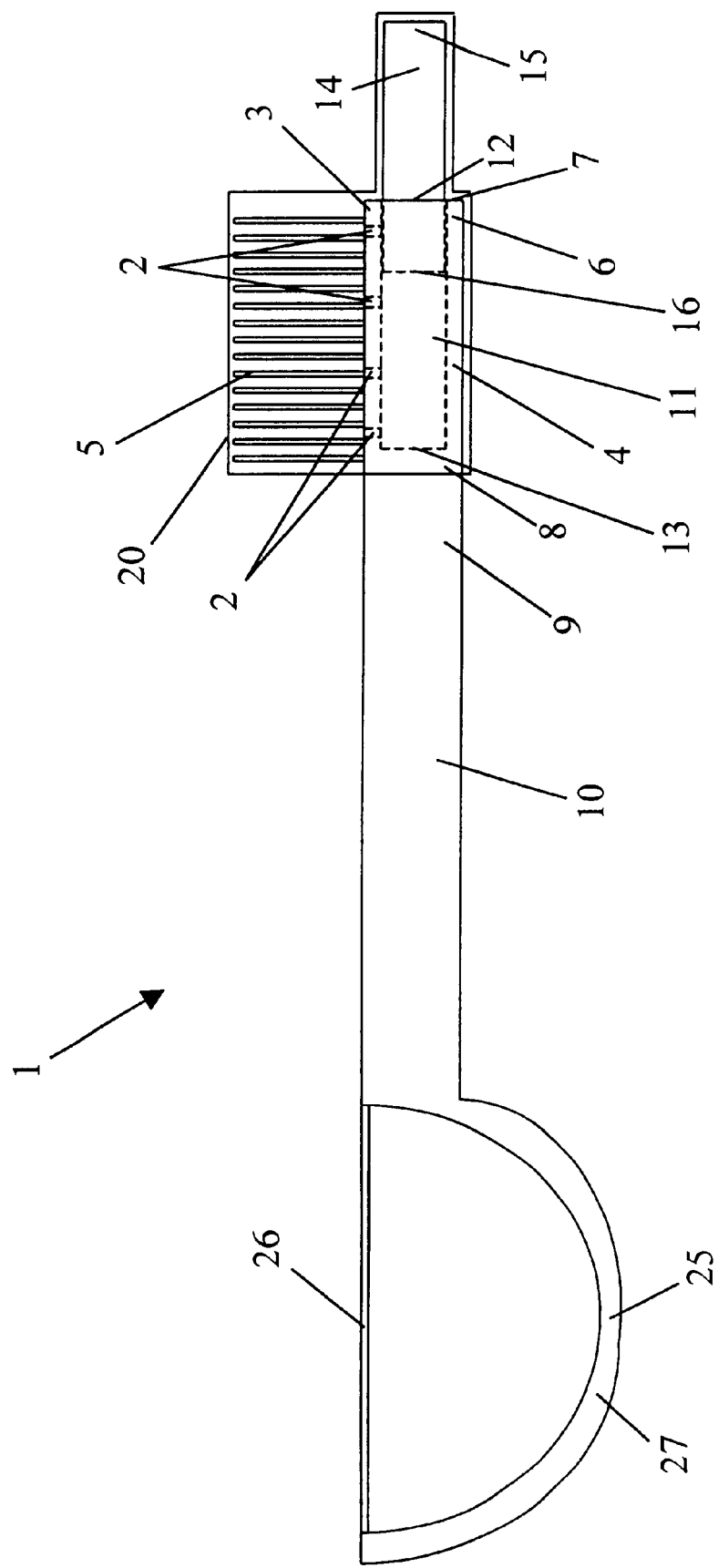
FIG. 2 is a lateral view of the first embodiment for the toothbrush.
Figure 3:
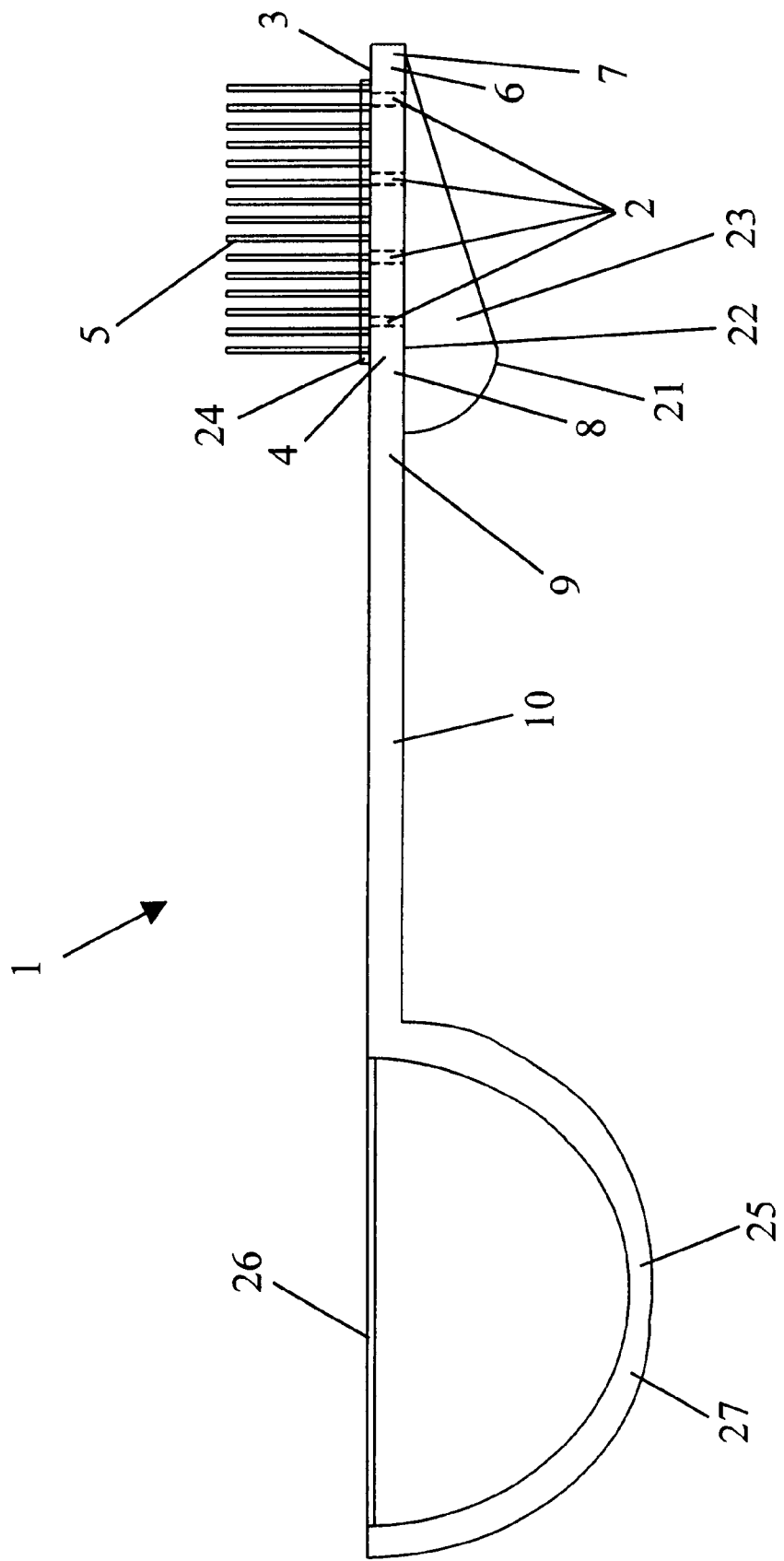
FIG. 3 is a lateral view of the second embodiment for the toothbrush.
Figure 4:
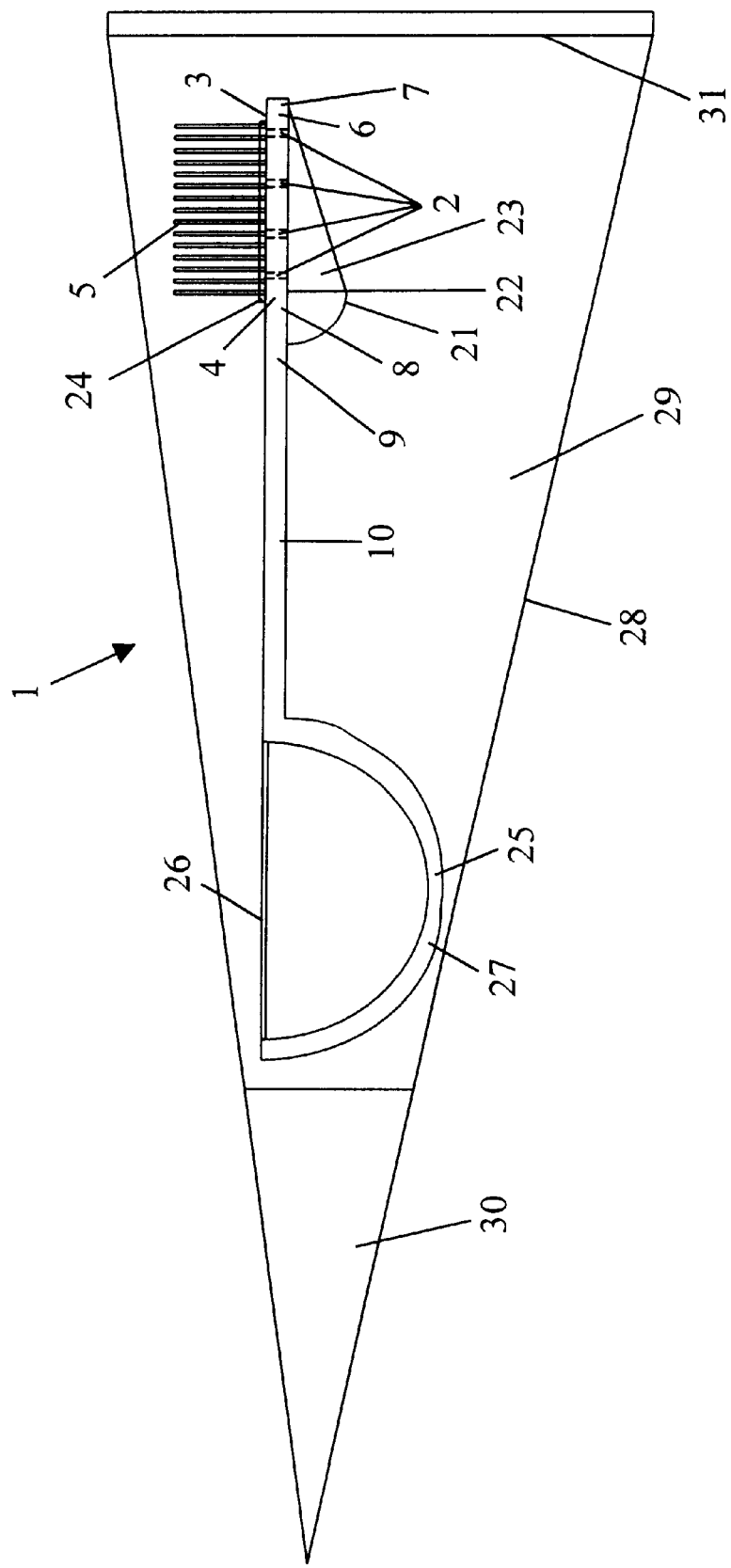
FIG. 4 portrays the packaging for the toothbrush.

As illustrated in FIGS. 1, 2 and 3, the toothbrush 1 of the present invention has one or more apertures 2 in a first side 3 of the head 4 of the toothbrush 1. Bristles 5 are attached to the first side 3. The head 4 is at a first end 6 of the toothbrush 1. A first end 7 of the head 4 is free, and a second end 8 of the head 4 is attached to a first end 9 of a body or handle 10 of the toothbrush 1.

In a first embodiment, illustrated by FIGS. 1 and 2, the one or more apertures 2 communicate with a chamber 11, which chamber is for containing toothpaste, within the head 4 of the toothbrush 1. The chamber 11 has an open end 12 and a closed end 13. The open end 12 of the chamber 11 is located at the first end 7 of the head 4.

A plunger 14 having a first end 15 and a second end 16 is slidably mounted within the chamber 11 with the first end 15 extending beyond the chamber 11 and the head 4 and with the second end 16 inside the chamber 11 so that as the second end 16 of the plunger 14 is forced farther into the chamber 11, toothpaste that has been placed within the chamber 11 is forced to flow through the aperture or apertures 2 onto the bristles 5.

Preferably, one or more folding flaps 17 attached to the plunger 14 will, as the second end 16 of the plunger 14 is moved from deeper within the chamber 11 to a position 18 near the open end 12 of the chamber 11, protrude into one or more channels 19 communicating with the chamber 11 to preclude the plunger 14 from being removed. The flaps 17 and channels 19 are constructed and angled such that the flaps 17 are merely pressed against the plunger 14 when the plunger 14 is pushed deeper into the chamber 11 away from the open end 12 of the chamber 11, thereby permitting the plunger 14 to move between the position 18 where the one or more folding flaps 17 protrude into the one or more channels 19 and the closed end 13 of the chamber 11. (Of course, when such folding flaps 17 are employed, toothpaste must be placed within the chamber 11 prior to insertion of the plunger 14.)

The head 4 of the toothbrush 1 and the plunger 14 will, in this first embodiment, preferably be sealed within a removable, preferably vacuum-sealed, wrapper 20 that covers the head 4 and the plunger 14 in order to keep the toothpaste fresh and prevent the plunger 14 from being pushed farther into the chamber 11 until it is desired to use the toothbrush 1.

In the second embodiment, which is shown in FIG. 3, a pliable pouch 21 for containing toothpaste is sealingly attached to a second side 22 of the head 4; and the apertures 2 run from the first side 3 of the head 4 to the second side 22 of the head 4. The cavity 23 created by the pouch 21 and head 4 is in communication with the one or more apertures 2. Thus, as one pushes the pouch 21 from outside the cavity 23, toothpaste that has been placed within the pouch 21 is forced to flow through the aperture or apertures 2 onto the bristles 5.

Preferably, with this second embodiment, a layer of material 24 that will rupture as toothpaste is forced toward the aperture or apertures 2 covers the aperture or apertures 2. Preferably, this layer of material 24 is on the second side 22 of the head 4, although it would be acceptable for the layer of material 24 to be on the first side 3 of the head 4. The pouch 21, the head 4, and the layer of material 24, consequently, tend to keep any toothpaste within the cavity 23 fresh. (Of course, toothpaste must be inserted into the cavity 23 before both the pouch 21 and the thin layer of material 24 have been installed.)

In either embodiment, a second end 25 of the handle 10 is curved and adapted in any manner that is well known in the art for attachment of dental floss 26 under tension so that such dental floss 26 spans the curve 27.

The packaging 28 for the toothbrush 1 has a first end 29 capable of containing the other elements of the toothbrush 1 and also capable of containing a liquid and also has a second end 30.

The second end 30 of the packaging 28 is removably attached to the first end 29 of the packaging 28 and is constructed, in any manner that is well known in the art, to contain powdered mouthwash. Optionally, the second end 30 of the packaging 28 is constructed, in any manner that is well known in the art, to contain gum, a breath mint, or a quantity of water.

The first end 29 of the packaging 28 is designed to contain the toothbrush 1 and can be opened and, preferably, releasably resealed. A preferred means for a reclosable seal 31 is a ZIPLOCK.

The second end 30 of the packaging 28 is removed from the packaging 28, the first end 29 of the packaging 28 is opened, the toothbrush 1 is removed from the first end 29, and the powdered mouthwash is placed with water into the first end 29 of the packaging 28. The first end 29 of the packaging 28 is then preferably resealed, and the first end 29 of the packaging 28 is shaken to encourage the powdered mouthwash to dissolve in the water. Finally, the first end 29 of the packaging 28 is opened to permit use of the mouthwash.

It should be noted that the term "preferably" (or any variant thereof) is used herein to denote a favored, but not necessary, structure.

We claim:

1. A toothbrush, which comprises:

a head having a first side containing at least one aperture, a free first end, a second end, a chamber having an open end located at the first end of said head and having a closed end and being in communication with the at least one apertures;

bristles attached to the first side of said head; a plunger having a first end and a second end slidably mounted within the chamber with the first end extending beyond the chamber and the head and with the second end inside the chamber; and a handle having a first end attached to the second end of said head, said handle also having a body portion extends from the second end of the head in the direction opposite to said plunger so as to be operatively held by a user and a second end attached to the body portion; and at least one folding flap attached to said plunger, wherein said head contains at least one channel communicating with the chamber and wherein said at least one flap and channel are constructed and angled so that said at least one flap protrude into said at least one channel as the second end of said plunger is moved from deep within the chamber to a position near the open end of the chamber to preclude said plunger from being removed and so that said at least one flap are merely pressed against said plunger when said plunger is pushed deeper into the chamber to dispense toothpaste.

2. The toothbrush as recited in claim 1, further comprising:

a removable wrapper covering and sealing said head and said plunger.

3. The toothbrush as recited in claim 2, wherein:

the second end of said handle is curved and adapted for attachment of dental floss under tension so that such dental floss spans the curved portion of the second end of said handle.

4. The toothbrush as recited in claim 3, further comprising:

packaging having a first end capable of containing the other elements of said toothbrush and also capable of containing a liquid, said packaging also having a second end, removably attached to the first end of said packaging, for containing powdered mouthwash, gum, a breath mint, or a quantity of water.

5. The toothbrush as recited in claim 4, wherein:

the first end of said packaging is resealable.

6. The toothbrush as recited in claim 2, further comprising:

packaging having a first end capable of containing the other elements of said toothbrush and also capable of containing a liquid, said packaging also having a second end, removably attached to the first end of said packaging, for containing powdered mouthwash, gum, a breath mint, or a quantity of water.

7. The toothbrush as recited in claim 6, wherein:

the first end of said packaging is resealable.

8. The toothbrush as recited in claim 1, wherein:

the second end of said handle is curved and adapted for attachment of dental floss under tension so that such dental floss spans the curved portion of the second end of said handle.

9. The toothbrush as recited in claim 8, further comprising:

packaging having a first end capable of containing the other elements of said toothbrush and also capable of containing a liquid, said packaging also having a second end, removably attached to the first end of said packaging, for containing powdered mouthwash, gum, a breath mint, or a quantity of water.

10. The toothbrush as recited in claim 9, wherein:

the first end of said packaging is resealable.

11. The toothbrush as recited in claim 1, further comprising:

packaging having a first end capable of containing the other elements of said toothbrush and also capable of containing a liquid, said packaging also having a second end, removably attached to the first end of said packaging, for containing powdered mouthwash, gum, a breath mint, or a quantity of water.

12. The toothbrush as recited in claim 11, wherein:

the first end of said packaging is resealable.

* * * * *